(12) United States Patent
Jackson

(10) Patent No.: US 6,773,460 B2
(45) Date of Patent: Aug. 10, 2004

(54) ANTERIOR VARIABLE EXPANDABLE FUSION CAGE

(76) Inventor: Roger P. Jackson, 6600 Indian Lane, Mission Hills, KS (US) 66208

( * ) Notice: Subject to any disclaimer, the term of this patent is extended or adjusted under 35 U.S.C. 154(b) by 0 days.

(21) Appl. No.: 09/729,758

(22) Filed: Dec. 5, 2000

(65) Prior Publication Data

US 2002/0068977 A1 Jun. 6, 2002

(51) Int. Cl.[7] .................................................. A61F 2/44
(52) U.S. Cl. ................................. 623/17.15; 623/17.11
(58) Field of Search ............................ 623/17.11, 17.12, 623/17.13, 17.14, 17.15, 17.16; 606/72, 73, 60, 61

(56) References Cited

U.S. PATENT DOCUMENTS

| | | | |
|---|---|---|---|
| 4,863,476 A | | 9/1989 | Shepperd |
| 5,489,210 A | * | 2/1996 | Hanosh ....................... 433/173 |
| 5,554,191 A | | 9/1996 | Lahille et al. |
| 5,609,635 A | * | 3/1997 | Michelson .................... 606/61 |
| 5,653,763 A | | 8/1997 | Errico et al. |
| 5,665,122 A | | 9/1997 | Kambin |
| 5,702,453 A | | 12/1997 | Rabbe et al. |
| 5,725,529 A | * | 3/1998 | Nicholson et al. ............ 606/72 |
| 5,776,197 A | | 7/1998 | Rabbe et al. |
| 5,776,198 A | | 7/1998 | Rabbe et al. |
| 5,782,832 A | * | 7/1998 | Larsen et al. ................. 606/61 |
| 5,782,865 A | * | 7/1998 | Grotz .......................... 606/232 |
| 5,957,953 A | * | 9/1999 | DiPoto et al. ............... 606/232 |
| 6,090,143 A | * | 7/2000 | Meriwether et al. ...... 623/17.11 |
| 6,102,950 A | * | 8/2000 | Vaccaro ....................... 606/61 |
| 6,165,219 A | * | 12/2000 | Kohrs et al. .............. 623/17.11 |
| 6,168,597 B1 | * | 1/2001 | Biedermann et al. ......... 606/73 |
| 6,206,922 B1 | * | 3/2001 | Zdeblick et al. .......... 623/17.11 |
| 6,214,007 B1 | * | 4/2001 | Anderson ..................... 606/73 |
| 6,500,205 B1 | * | 12/2002 | Michelson ............... 623/17.16 |

FOREIGN PATENT DOCUMENTS

WO     WO 00/12033 A1 * 3/2000 ............. A61F/2/44

* cited by examiner

Primary Examiner—David Isabella
Assistant Examiner—Urmi Chattopadhyay
(74) Attorney, Agent, or Firm—John C. McMahon

(57) ABSTRACT

An interbody device for use between a pair of adjacent vertebrae includes a body and at least one expansion member. The body has upper and lower walls that are joined by a rear wall that functions as a spring hinge. The walls have anterior ends that are supported in a non-expanded configuration by spaced feet that project out from the walls. The expansion member is elongate and has a threaded portion that is threadably received in the rear wall. Each expansion member also includes a head having a wedge portion that engages the anterior ends of the walls and forces the walls apart as the expansion member is screwed into the body. Preferably, the expansion member is only one of a plurality of expansion members found in a kit which vary with respect to the diameter of the expansion member head. Further, a support and connecting plate is preferably utilized subsequent to installation of the devices between vertebrae to connect the connected pair of the devices.

19 Claims, 4 Drawing Sheets

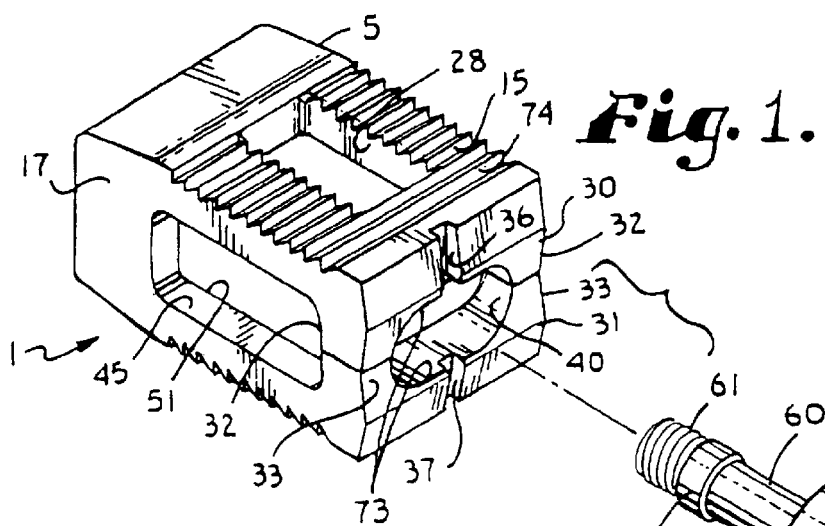
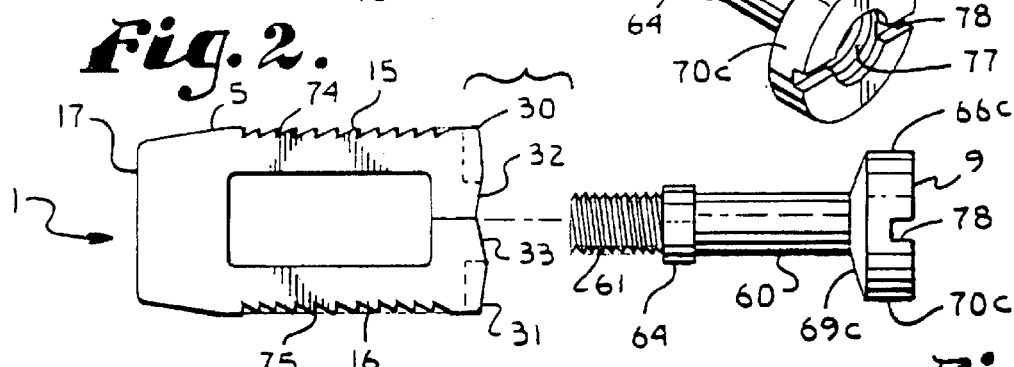
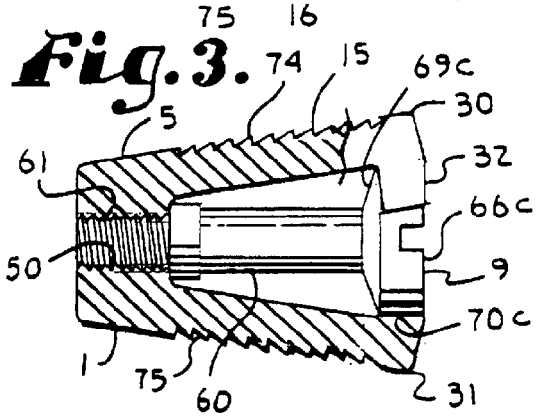
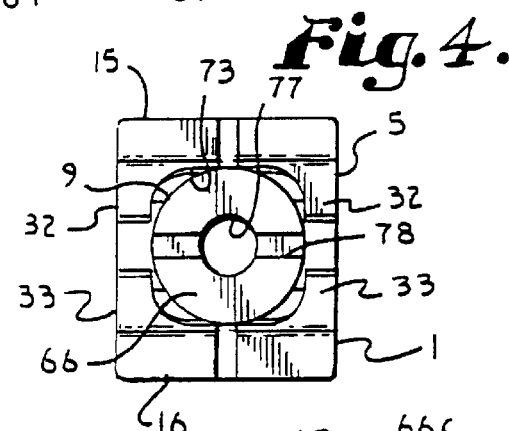
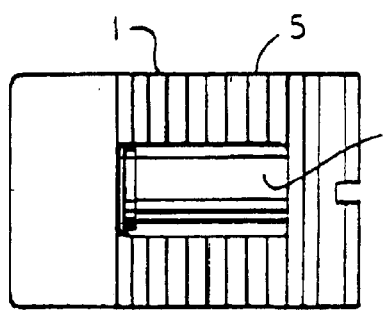
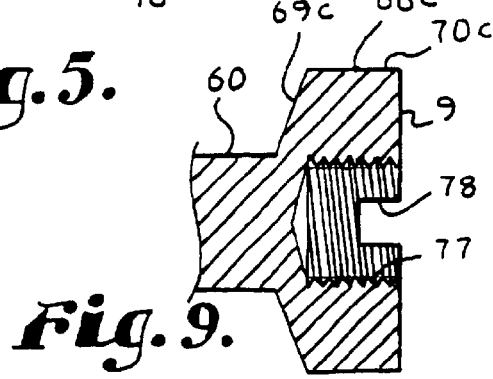

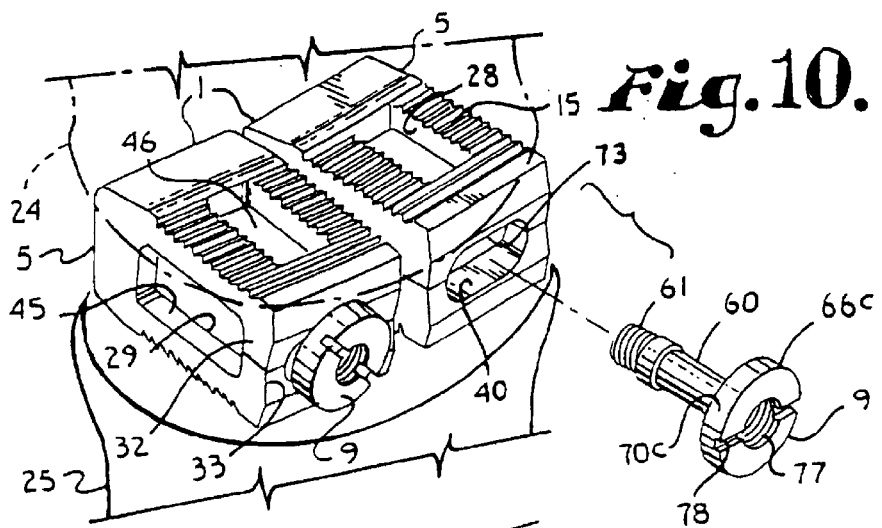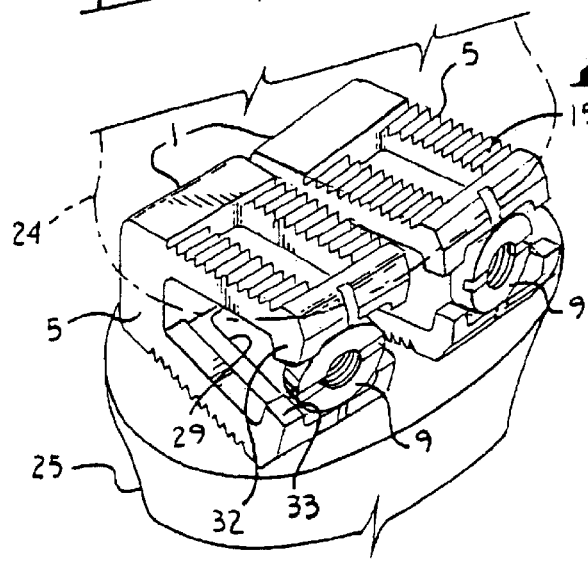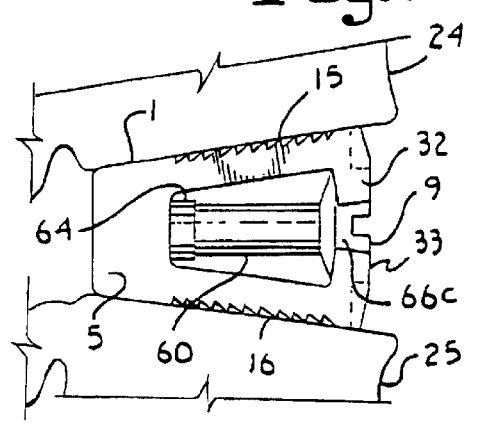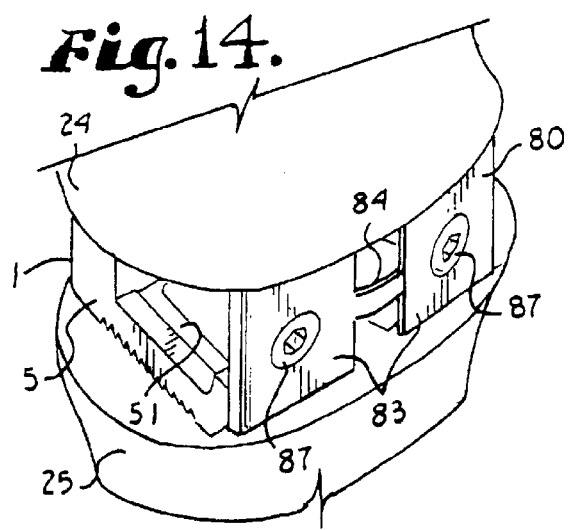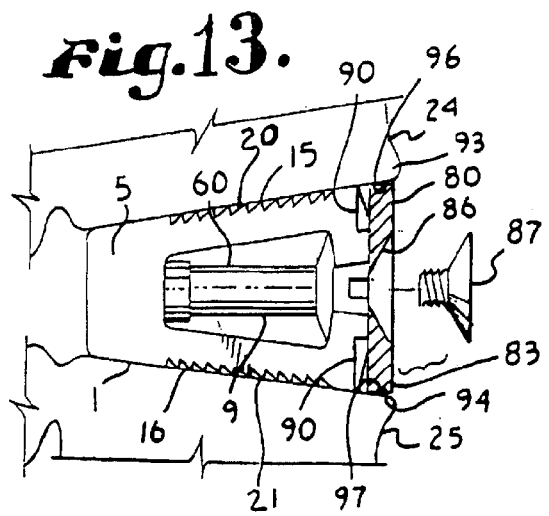

ANTERIOR VARIABLE EXPANDABLE FUSION CAGE

BACKGROUND OF THE INVENTION

Fusion cages, as well as related interbody devices, are frequently utilized in spinal surgery between vertebrae of a patient. In particular, one or a pair of interbody devices are placed between the vertebrae to provide support and promote fusion between vertebrae where such is necessary due to disease, injury, general deterioration or a congenital problem. Frequently, the anterior sides or fronts of the vertebrae also require additional spacing in comparison to posterior sides. Therefore, it is often desirable to use an anteriorly expandable interbody device so that the vertebrae are spread or spaced more on the anterior sides thereof than on the posterior sides thereof. It is seldom if ever desirable to space the posterior sides of the vertebrae more than the anterior sides thereof. Interbody devices which provide for anterior greater expansion are generally referred to as interbody expansion devices or expansion cages. These cages are specifically expandable on the anterior end thereof, so that the fronts of the adjacent vertebrae between which the cages are located are more greatly spaced than the rears.

It is noted that interbody devices, such as fusion cages, may be inserted into the intervertebral space anteriorly or posteriorly. The present application is directed to the types of devices that are inserted anteriorly or from the front of the patient and are generally referred to as anterior interbody devices or anterior fusion cages.

Interbody devices typically must be very strong along the entire length of the top and bottom walls of the device that engage the vertebrae. In particular, in the turning and twisting of everyday life, substantial forces can be exerted against the interbody devices and, in particular, against one end or the other thereof. This is even more the case when the devices are subjected to unusual forces during an accident or the like. Some types of interbody devices in the prior art have provided for anterior expansion, but have not well supported the anterior end of the upper and lower walls. Such prior art devices have sometimes provided some kind of a wedge or rod that is urged axially along a ramp of the device in such a way as to expand the anterior portion subsequent to the cage being placed between the vertebrae. Because the wedge moves rearwardly or posteriorly toward the back wall of the device in order to spread the walls, a lever arm of unsupported wall is formed between the front edge of each wall and the position where the wedge engages the walls. Substantial forces can act on this lever arm. The interbody devices poorly supported along the unsupported wall can then fail due to forces exerted along the lever arm in the region.

Secondly, it is desirable that the interbody devices do not expand sideways while they are expanding vertically. This need arises because it is often necessary to put interbody devices in close proximity to one another in side by side relationship. Sideways expansion may prevent desirable positioning of the interbody devices and may also interfere with positioning of bone chips for grafting between the interbody devices.

When installing interbody devices, such as fusion cages, or even after an initial expansion a surgeon may also find that it is necessary to have more anterior expansion than was initially anticipated. Consequently, it is often desirable to have a variable expansion cage be able to increase the expansion in increments that allow the surgeon to determine if expansion is sufficient with each advance in expansion and thereafter go to a greater expansion, if necessary.

Finally, interbody devices, such as fusion cages, are quite expensive to produce in general. This is because the body of the devices must be made to very high tolerances in order to provide reproducible results and to provide the strength necessary to support the spine of the person. Because the surgeon is not always certain exactly which expansion size interbody device will be required until the surgery site is opened, it has been necessary for the surgeon to have on hand many different sizes of fusion cages and, in some cases, different types of fusion cages so as to insure that the necessary item will be present when the surgery is performed.

Consequently, it is also desirable to be able to provide an interbody device that is modular in nature in that it may be used as efficiently with no expansion as with expansion and the same device can be used with different degrees of expansion. Many of the expandable types of prior art fusion cages cannot be used as non-expandable type cages.

Further, it is desirable that a single fusion cage body be usable for virtually any degree of expansion desired or foreseeable by simply providing a set of comparatively much less expensive expansion members, any of which may be used in conjunction with the body to provide for various and different degrees of expansion.

SUMMARY OF THE INVENTION

An interbody device or fusion cage for use between a pair of adjacent vertebrae in order to provide support and/or promote growth between the vertebrae that have been destabilized due to injury, illness or the like. The interbody device includes a body which may be of different types, including bodies rectangular in shape, in which case the device is slid or driven between the vertebrae, or generally cylindrical in shape and threaded, in which case the device is screwed between the vertebrae. The body has an upper wall and a lower wall that are connected by a rear or posterior wall. The body is hinged about the rear wall by utilization of a material of construction that is flexible or resilient such as stainless steel or titanium, so that the upper and lower walls are able to pivot relative to each other at the rear, when a spreading force is applied to the walls, so that anterior ends of the walls rotate from an initial non-expanded configuration anteriorly to an expanded configuration anteriorly. Unless a spreading force is applied, the upper and lower walls are urged to remain generally parallel to each other.

The upper and lower walls also have legs on either side of the anterior end thereof that face toward similarly positioned legs on the other wall and which abut against each other when the device is in the unexpanded configuration thereof. An aperture is formed between the legs and preferably extends through the body in such a manner so as to form an interior chamber suitable for receiving bone chips or other growth promoting media. The body also preferably has upper and lower windows which communicate with the chamber and open onto the surface of the bones, when in use, so as to promote growth of the bone through the interbody device. The rear wall of the body includes a threaded bore.

An expansion member, preferably having a shape similar to a large headed bolt, is utilized to apply spreading force to the upper and lower walls so as to expand the body anterior end. The point or region of engagement between the expansion member and cage walls preferably remains the same throughout the expansion process by use of a wedge surface on the expansion member and is located near the anterior end of the cage. The expansion member includes an elongate shaft threaded on one end so as to be operably and threadably received in the rear wall bore and having a head at an opposite end. The shank includes a stop, preferably a section of the shank of enlarged diameter compared to and adjacent to the threaded end, which insures that the expansion member is properly positioned during use.

The expansion member head includes a first wedge surface that slopes radially outward and frontwardly relative to the remainder of the shank near an anterior end of the shank. The wedge surface preferably has the shape of a truncated cone. The wedge surface is sized, and shaped in position so as to engage a wedge mating edge or surface located on each of the lower and upper walls. In particular, the wedge surface first engages the mating surfaces on the walls at the posterior end of the wedge surface and then the mating surface slides along the wedge surface as the expansion member is screwed into the rear wall bore. In this manner the anterior end of the body is forced to spread or space vertically until a forward or anterior end of the edge of the wedge surface is reached. The wedge surface is adjacent to a generally cylindrical shaped support surface and transfers the support of the upper and lower walls to the cylindrical shaped surface as the expansion member is further rotated clockwise and advanced into the rear wall bore. The cylindrical support surface is preferably coaxial with an axis of rotation of the expansion member such that continued advancement of the expansion member to the stop causes the support surface to pass between the anterior ends of the upper and lower walls and to thereafter provide support to the upper and lower walls and keep the walls in a selected spaced relationship relative to each other.

In certain embodiments of the invention wherein the interbody device is rectangular in shape, a pair of side by side cages may be integrally joined or joined together by fasteners in order to form a single operative unit which preferably requires a pair of expansion members, but which may also use a single expansion member.

Furthermore, the devices, when used in side by side pairings, are frequently joined by a connector so as to further assure the stability of the devices. Also preferably, the connector extends between a relatively hard bony region associated with the anterior ends of the vertebrae so as to provide extra support in that region and resist subsidence of the vertebrae relative to the interbody devices.

Finally, in use each interbody device is normally provided with a set of expansion members wherein each member of the set provides a different degree of spacing of the anterior end of the interbody device. In this manner, a surgeon can utilize the interbody device without an expansion member or can alternatively select from a number of different sized expansion members to provide appropriate expansion of the anterior end of the interbody device. Normally, the surgeon would start with no or minimal expansion and then increase incrementally toward greater expansions by removal of less expanding devices and replacement by greater expanding devices until the surgeon is satisfied with the expansion provided.

OBJECTS AND ADVANTAGES OF THE INVENTION

Therefore, the objects of the present invention are: to provide an interbody device or fusion cage for use between a pair of vertebrae that is expandable; to provide such an interbody device that has a body and at least one expansion member wherein the expansion member or body has a wedge surface that engages an anterior portion of upper and lower walls of the body so as to spread the body from near the anterior end thereof; to provide such a device wherein a single body may be utilized either without an expansion member or in conjunction with any of an alternative group of modular expansion members each producing a different degree of expansion contained in a kit of expansion members; to provide such a device wherein an expansion member providing one degree of expansion can be removed and an expansion member providing a greater degree of expansion can be subsequently inserted; to provide such a device wherein the expansion members include an anterior or frontward cylindrical surface upon which anterior portions of the upper and lower body walls rest subsequent to full insertion of the expansion member; to provide such a device wherein the device expands vertically and not horizontally or side to side; to provide such a device wherein a pair of units may be joined into a single device and expanded by one or more expansion members; to provide such a device including a central cavity and windows to allow for packing with bone chips or other growth media so as to promote fusion between adjacent vertebrae exposed to the windows; to provide such a device wherein a single body may be utilized with a number of different expansion members, such that bodies of multiple different sized are not required to be maintained in stock during a surgical operation installing such devices; to provide such a device that does not cantilever the walls over a wedge that is medially located with respect to the body, but rather positions the wedge surface and the support surface at all times during expansion near the anterior end of the body so as to continuously provide support to anterior ends of the walls; to provide such a device that does not expand horizontally as the device expands vertically; and to provide such a device which is relatively inexpensive to produce, extremely easy to use and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective and exploded view of an expandable, anterior interbody fusion device, illustrating a body of the device in a non-expanded configuration and an expansion member.

FIG. 2 is a side elevational and exploded view of the body in a non-expanded configuration and the expansion member.

FIG. 3 is a side elevational view of the body and expansion member joined together with portions removed to show interior detail thereof.

FIG. 4 is a front elevational view of the body with the expansion member inserted therein and in an expanded configuration thereof.

FIG. 5 is a top plan view of the body with the expansion member inserted therein.

FIG. 9 is an enlarged and fragmentary cross-sectional view of the third expansion member, taken along line 9—9 of FIG. 8.

FIG. 10 is a perspective and partly exploded view of a pair of interbody devices of the type shown in FIG. 1 positioned between a pair of vertebrae, with the top vertebrae shown in phantom, and showing the expansion member on the left hand side being inserted in a respective body with a wedge thereof just engaging upper and lower walls of the body and further, with an expansion member on the right-hand side outside of the body.

FIG. 11 is a perspective view of the interbody devices and vertebrae similar to the view of FIG. 10 except both expansion members have been fully inserted in the bodies and the bodies have been anteriorly expanded.

FIG. 12 is a side elevational view of the interbody devices and vertebrae in the configuration seen in FIG. 11 with an expansion member fully inserted in a body and with the body expanded to anteriorly space vertebrae associated therewith.

FIG. 13 is a side elevational and partly exploded view of one of the interbody devices between the vertebrae with the body thereof expanded by an expansion member and showing a frontward connecting plate being joined thereto by a set screw.

FIG. 14 is a perspective view of the interbody devices positioned between the vertebrae with the connecting plate joined thereto.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 6:
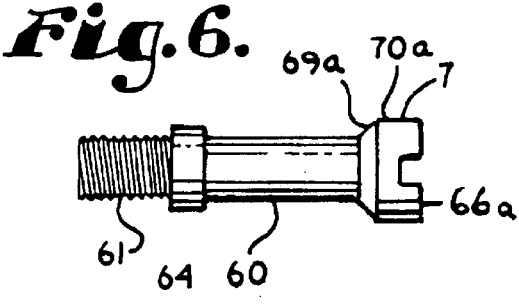
FIG. 6 is a side elevational view of a first expansion member.
Figure 6A:
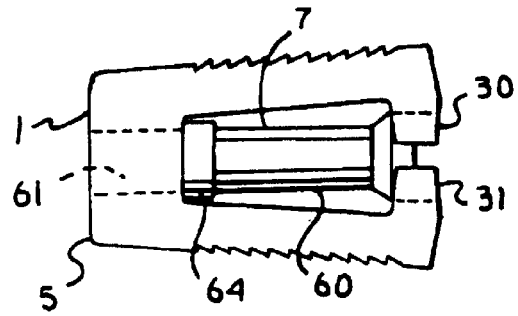
FIG. 6a is a side elevational view of the body with the first expansion member inserted therein.

The reference numeral 1 generally designates an interbody device or fusion cage in accordance with the present invention seen in FIGS. 1 to 14. The device 1 includes a body 5 and a set of expansion members including expansion members 7, 8 and 9. The expansion member 9 is the largest of the set and is seen in FIGS. 1 through 5 as well in FIGS. 8 and 8a. The expansion member 7 is the smallest of the group and is seen in FIGS. 6 and 6a. Although only three expansion members are shown in the present embodiment and together with the body 5 form a kit for use in spinal surgery, it is foreseen that a much larger group of expansion members, each having a different head diameter or expansion capability, could be included in the kit with small degrees of separation between the size thereof. In some situations the kit may include only two expansion members.

The body 5 includes a top or upper wall 15, a bottom or lower wall 16 and a posterior or rear wall 17. The upper wall 15 and lower wall 16 are joined near the posterior ends thereof to the rear wall 17. As used herein posterior and anterior pertain to configurations in the human body and posterior would be to the left in FIG. 2, while anterior would be to the right in FIG. 2. The upper wall 15 and lower wall 16 are initially in generally parallel relationship to one another and are urged to that position by the springy or resilient nature of materials of construction thereof that try to maintain the non-expanded shape thereof unless force is applied to change that shape. Preferably the body 5 is constructed of a bio-compatible metal or the like such as stainless steel or titanium and the rear wall acts as a spring to try to maintain the upper wall and lower wall 15 and 16 in parallel relationship, while also functioning as a hinge, when the two walls 15 and 16 are forced apart opposite the rear wall 17 by application of spreading force to the walls 15 and 16.

The upper and lower walls 15 and 16 have bone engaging outer surfaces 20 and 21 which are serrated in such a manner as to bite into the bone of vertebrae 24 and 25 respectively, after being placed therebetween. The upper and lower walls 15 and 16 also have fenestration or a window 28 and 29 respectively. Although the present embodiment is shown with single windows 28 and 29, it is foreseen in some circumstances that no windows would be provided and in other circumstances multiple windows may be provided along the walls 15 and 16.

Near the anterior end 30 and 31 of each of the walls 15 and 16 and located on either side thereof are a pair of legs 32 and 33 respectively. The legs 32 and 33 of each of the walls 15 and 16 extend toward one another and respective pair of legs 32 and legs 33 abut when the body 5 is in a non-expanded configuration thereof, such as is shown in FIG. 1. In this manner the front or anterior ends 30 and 31 of the walls 15 and 16 are supported by the legs 32 and 33 in the non-expanded configuration. Vertical slots 36 and 37 are medially formed in the walls' anterior ends 30 and 31. An aperture 40 is located between the sets of legs 32 and 33 and is a somewhat elongate oval shaped slot which alternatively receives the expansion members 7, 8 or 9, as is noted below. Immediately located along and between the walls 15 and 16 are a pair of side windows 45 and 46.

The rear wall 17 includes a centrally located threaded bore 50. A bone chip receiving cavity 51 is located between the walls 15, 16 and 17.

Each of the expansion members 7, 8 and 9 include an elongate shank 60 having a threaded posterior portion 61 that is sized and shaped to be received in the rear wall threaded bore 50. Each shank 60 also has a stop 64 that is a region of increased diameter located at the forward end of the posterior threaded portion 61 thereof. Each of the expansion members 7, 8 and 9 also include a head generally identified as the number 66.

The expansion member 7 has a head 66a, the expansion member 8 has a head 66b and the expansion member 9 has a head 66c. The heads 66a, 66b, and 66c each include a rearward wedge shaped surface and a support surface which in each case is identified by the reference numerals 69 and 70 respectively along with the letter identifying the particular head associated therewith. The wedge shaped surfaces 69 are generally in the shape of a truncated cone. The support surfaces 70 are generally in the shape of a cylindrical surface. In each case the surfaces 69 and 70 are coaxial with an axis of rotation A associated with each of the expansion members 7, 8 and 9. During installation of the expansion members 7, 8 or 9 into the body 5, the associated wedge shaped surface 69 engages a wedge mating receiver that is a surface or edge 73. While the present embodiment illustrates the edge 73 as being linear, it is foreseen that an angled planar surface could function for this purpose also. The support surfaces 70 in turn engage and support facing surfaces 74 of wall 15 and surface 75 of wall 16. Preferably the surfaces 74 and 75 extend approximately the width of the head support surface 70.

Figure 7:
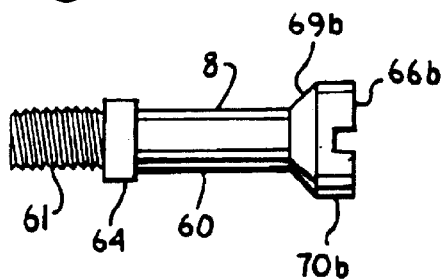
FIG. 7 is a side elevational view of a second expansion member.
Figure 7A:
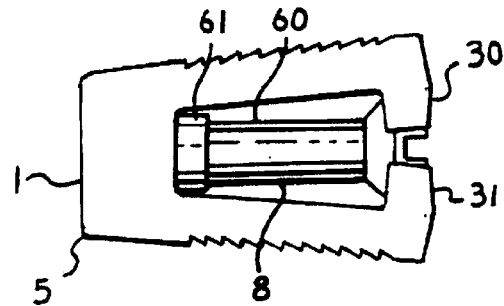
FIG. 7a is a side elevational view of the body with the second expansion member inserted therein.
Figure 8:
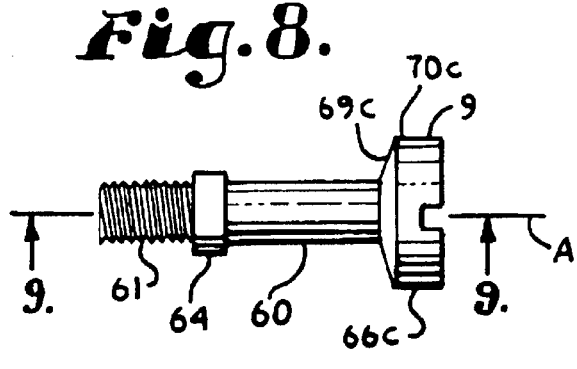
FIG. 8 is a side elevational view of a third expansion member which is the expansion member shown in FIGS. 1 through 5.
Figure 8A:
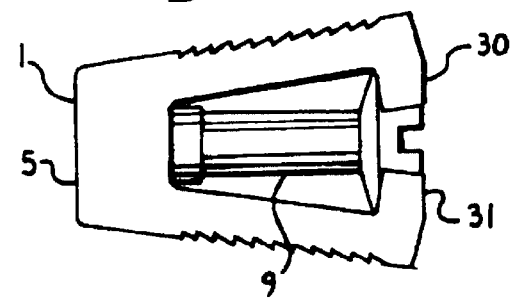
FIG. 8a is a side elevational view of the body with the third expansion member received therein.

As seen in FIGS. 6 through 8, the heads 66a, b and c of each of the expansion members 7, 8 and 9 increase progressively in diameter. In this manner the expansion members 7, 8 and 9 provide increasing expansion of the anterior ends 30 and 31 of the body, as is seen in FIGS. 6a through 8a, when fully inserted therein into the body 5. A connecting and supporting plate 80 is preferably utilized to join a pair of devices 1 together in the manner shown in FIG. 14. The plate 80 includes a pair of panels 83 connected by a rod 84. The panels 83 have a centrally located and countersunk aperture 86 which receives a set screw 87 which is in turn seated in threaded bores 77 in the expansion members 7, 8 or 9. Each of the panels 83 also includes a pair of lugs 90 that mate with the body slots 36 and 37. The purpose of the connecting plate 80 is both to provide greater stability to the devices 1 and to provide upper and lower surfaces 93 and 94 that operably engage anterior comparatively hard bony surfaces 96 and 97 of the vertebrae 24 and 25 in order to resist subsidence of the vertebrae 24 and 25 relative to the devices 1.

In use the pad or disc located between a pair of vertebrae 24 and 25 is removed and a pair of the bodies 5 are inserted in the manner shown in FIG. 10. Preferably, the bodies 5 are not positioned exactly parallel to one another, but rather at slight angles relative to one another to better resist against the bodies 5 being inadvertently removed during usage. Once the bodies 5 have been positioned between the vertebrae 24 and 25, the surgeon checks to determine whether anterior expansion is desirable. If expansion is needed, normally the expansion member having the smallest diameter, in this case expansion member 7, is inserted in each of the bodies 5 and screwed into place. As the members 7 are screwed inwardly, the wedge shaped surface 69a engages and biases against the mating surface or edge 73 of the upper and lower walls 15 and 16 so as to space the anterior ends 30 and 31 of the upper wall and lower walls 15 and 16 respectively. The surgeon then determines whether or not additional anterior expansion is required. If so, the first expansion member 7 is removed from each of the bodies 5 and a second expansion member of somewhat larger diameter, such as expansion member 8 is installed. This process is continued until the surgeon is satisfied that the proper expansion has been achieved. Subsequently, the connecting plate 80 that is sized and shaped for a respective expansion member 7, 8 or 9 is secured to the bodies 5 by using the set screws 87.

Illustrated in FIGS. 15 through 19 is a second modified embodiment of an interbody device in accordance with the present invention, generally identified by the reference numeral 100. The device 100 includes a unitary body 105 and at least a pair of expansion members 107. The device 100 is similar in many ways to the device 1 and consequently, the similarities will not be discussed in great detail. The major difference between the device 100 and the device 1 is that the device 100 is essentially a pair of the devices 1 that have been joined together in side by side relationship with unnecessary structure removed. Each of the devices 100 include an upper wall 115, a lower wall 116 and a rear wall 117. The rear wall 117 functions as both a spring hinge to urge the walls 115 and 116 into parallel relationship with one another and to also allow anterior ends 130 and 131 of the walls 115 and 116 respectively to expand when the expansion members 107 are inserted therein.

Figure 15:
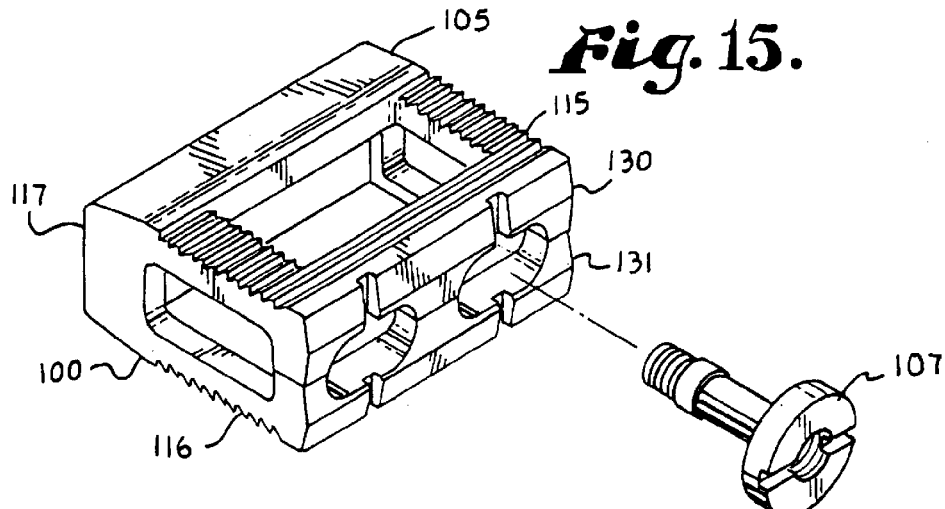
FIG. 15 is a perspective and partly exploded view of a first modified interbody device having the overall length equivalent to a pair of the devices of the type shown in FIG. 1 and utilizing a pair of expansion members.
Figure 16:
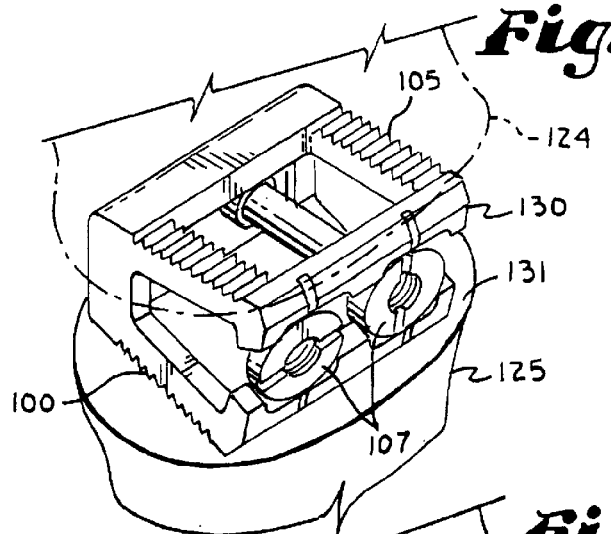
FIG. 16 is a perspective view of the modified interbody device showing a pair of expansion members fully positioned therein and with an anterior end of the device in an expanded configuration.
Figure 17:
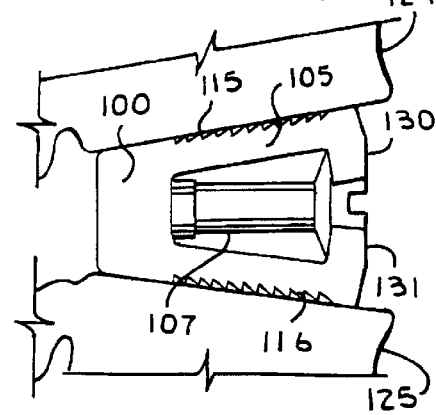
FIG. 17 is a side elevational view of the modified interbody device with the expansion members therein and expanded so as to space anterior ends of the vertebrae more than the posterior ends thereof.

FIG. 16 illustrates the device 100 located between a pair of vertebrae 124 and 125 with the expansion members 107 fully positioned within the body 105 and within anterior ends 130 and 131 expanded as compared to a non-expanded configuration, as is shown in FIG. 15.

Figure 19:
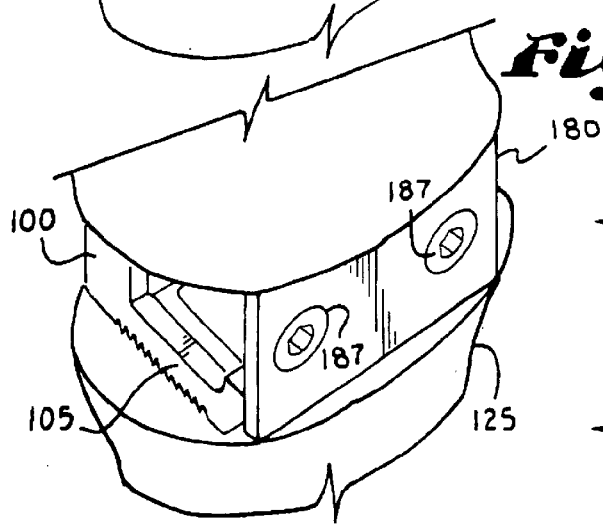
FIG. 19 is a perspective view of the modified device between a pair of vertebrae with the connecting plate joined thereto.
Figure 18:
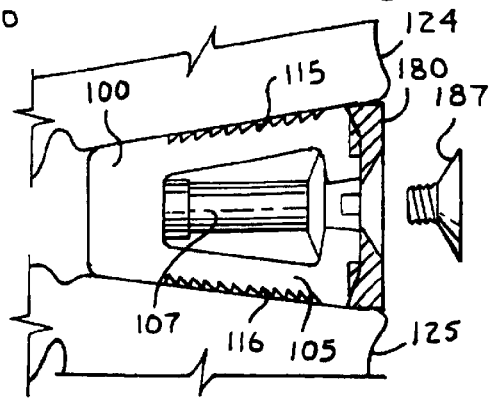
FIG. 18 is a side elevational and partly exploded view similar to FIG. 17 except with a support plate being shown joined to the modified device and with a set screw in a position to connect the plate to the modified device.

A solid support and connecting plate 180 is joined to the device 100 by a pair of set screws 187, as is seen in FIG. 19.

The device 100 is used in a similar manner to the device 1, except that only a single device 100 is utilized between a pair of vertebrae 124 and 125. As with the previous embodiment, expansion members having a size other than the illustrated expansion member 107 may be utilized in order to provide different degrees of expansion of the device 100, so that the device 100 has a plurality of expanded configurations available thereto, as well as the unexpanded configuration shown in FIG. 15.

It is also foreseen that the expansion members may be of varying types under the invention. For example, the heads of the expansion members may have opposed sectors removed so as to mate with an insertion tool replacing such sectors. In this way the tool may be used to insert the expansion members and then removed with the remaining sectors used to support the opposed walls of the cage body. A rod can also be used with such cages that is inset in a channel in the front of the expansion member to prevent them from turning after insertion is complete and can be elongate to two of the bodies for greater stability. Such rods are held in the expansion members by set screws in bores intersecting with the rod channels.

It is to be understood that while certain forms of the present invention have been illustrated and described herein, it is not to be limited to the specific forms or arrangement of parts described and shown.

What is claimed and desired to be secured by Letters Patent is as follows:

1. An anterior interbody device that is anteriorly variably expandable; said device comprising:

a) a U-shaped body having an upper wall and a lower wall hingeably joined by a rear wall; said body having a threaded bore, said upper and lower walls having a non-spaced configuration wherein anterior ends of said upper and lower walls are in close proximity to each other;

b) said upper and lower walls each having an anterior end and an anterior wedge mating receiver that face each other;
c) an elongate expansion member; said expansion member being threaded and being threadedly received in said body bore;
d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration; said upper and lower anterior wedge mating receivers engaging and being supported by said expansion member at the anterior ends of said walls in close proximity to a front of said device after said anterior ends of said walls are placed in said spaced configuration; said body bore is located in said rear wall and threadedly engages said expansion member.

2. The device according to claim 1 wherein:
a) said expansion member has an axis of rotation; and
b) said wedge surface has a truncated coaxial shape and is coaxial with said axis of rotation.

3. The device according to claim 1 wherein:
a) said upper and lower walls each include a window positioned to allow growth of bone therethrough during usage.

4. The device according to claim 1 wherein:
a) said wedge mating receiver is an edge that is positioned to extend from side to side relative to and be spaced from an axis of rotation of said expansion member.

5. In an expandable anterior interbody fusion cage; the improvement comprising:
a) said cage having a U-shaped body having a rear wall and having upper and lower walls each with an anterior end and an anterior wedge mating receiver; and
b) an elongate expansion member that is threadedly received in said rear wall of said body and which has a head with an anterior wedge shaped surface for operably engaging said body wedge mating receivers and expanding an anterior end of said cage as said expansion member advances into said body; subsequent to said expansion member being fully in position to space anterior ends of said walls, said head being sized and positioned to remain in contact with and supporting the anterior ends of said walls in close proximity to a front of said cage.

6. In an expandable fusion cage having a first expansion member; the improvement comprising:
a) an expansion kit including at least said first expansion member and a second expansion member that is interchangeable with said first expansion member; each of said expansion members being cooperatively mateable with said cage to provide a different degree of anterior expansion of said cage; and each of said expansion members including a shank that operably mates with said cage and a wedge that is integral with said shank.

7. An anterior interbody device that is anteriorly variably expandable; said device comprising:
a) a U-shaped body having an upper wall and a lower wall hingeably joined by a rear wall; said body having a threaded bore, said upper and lower walls having a non-spaced configuration wherein anterior ends of said upper and lower walls are in close proximity to each other;
b) said upper and lower walls each having an anterior wedge mating receiver that face each other;
c) first and second elongate expansion members; each of said expansion members being threaded and being threadedly received in said body bore;
d) each of said expansion members having an anterior wedge surface that is sized, shaped and positioned to engage said upper and lower anterior wedge mating receivers as a selected one of said first and second expansion members is threadedly advanced into said body bore, such that anterior ends of upper and lower walls are placed in a spaced configuration wherein said upper and lower walls become spaced greater than said non-spaced configuration; and
e) said first and second expansion members each having a support surface anterior of said wedge surface; each of said support surfaces being cylindrical in shape; each of said support surfaces having different diameters so that said first and second expansion members can be selectively individually used with said body to produce different degrees of expansion of the anterior end of said body.

8. An anterior interbody device that is anteriorly variably expandable; said device comprising:
a) a U-shaped body having an upper wall and a lower wall hingeably joined by a rear wall; said body having a threaded bore, said upper and lower walls having a non-spaced configuration wherein anterior ends of said upper and lower walls are in close proximity to each other;
b) said upper and lower walls each having an anterior wedge mating receiver that face each other;
c) an elongate expansion member; said expansion member being threaded and being threadedly received in said body bore;
d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration;
e) said expansion member having an axis of rotation;
f) said expansion member having a threaded region near a posterior end thereof that is mateable with said body bore;
g) said expansion member having a head near an anterior end thereof; said head including said wedge surface in the shape of a truncated cone; said head including a cylindrical supporting surface anterior of said wedge surface that is sized, shaped and positioned to engage and support said upper and lower walls when said expansion member is fully inserted into said body; said U-shaped body being sufficiently flexible so that as said expansion member is threadedly advanced into said body, said wedge surface engages said upper and lower wall wedge mating receivers and spreads the anterior ends of said upper and lower walls while flexing at a posterior end of said walls and, thereafter said support surface engages and supports said upper and lower walls in a preselected anterior spaced configuration; and
h) said expansion member including a stop located to position said expansion member in said body.

9. The device according to claim 8 wherein:
a) said stop is a region along said expansion member anterior of said threaded region and having a greater diameter than said threaded region.

10. An anterior interbody implant having first and second interbody devices that are anteriorly variably expandable; each of said first and second devices comprising:
a) a U-shaped body having an upper wall and a lower wall hingeably joined by a rear wall; each of said upper and lower walls having an anterior end; said body having a threaded bore located in said rear wall, said upper and lower walls having a non-spaced configuration wherein anterior ends of said upper and lower walls are in close proximity to each other;
b) said upper and lower walls each having an anterior wedge mating receiver that face each other;
c) an elongate expansion member; said expansion member being threaded and being threadedly received in said body bore;
d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration; said expansion member remaining in contact with and supporting the anterior ends of said walls in close proximity to a front of said implant, when said walls are in the spaced configuration thereof; and said implant further including
e) a connector for joining said first and second devices in close proximity to one another during use.

11. The device according to claim 10 wherein:
a) said connector is a plate sized and shaped to engage anterior portions of vertebrae when the first and second devices are located between the vertebrae during use to provide additional support to said vertebrae.

12. An anterior interbody device that is anteriorly variably expandable; said device comprising:
a) a U-shaped body having an upper wall and a lower wall hingeably joined by a rear wall; said body having a threaded bore located in said rear wall, said upper and lower walls having a non-spaced configuration wherein anterior ends of said upper and lower walls are in close proximity to each other;
b) said body being generally rectangular in cross section;
c) said upper and lower walls each having an anterior end and an anterior wedge mating receiver that face each other;
d) an elongate expansion member; said expansion member being threaded and being threadedly received in said body bore; and
e) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration; said expansion member remaining in contact with and supporting the anterior ends of said walls in close proximity to a front of said device in the spaced configuration thereof.

13. An anterior interbody device that is anteriorly variably expandable; said device comprising:
a) a U-shaped body having an upper wall and a lower wall hingeably joined by a rear wall; said body having a threaded bore, said upper and lower walls having a non-spaced configuration wherein anterior ends of said upper and lower walls are in close proximity to each other;
b) said upper and lower walls each having an anterior wedge mating receiver that face each other;
c) said upper and lower walls having anterior surfaces that engage when in a non-expanded configuration such that said device is adapted to be utilized alternatively as an expanded or non-expanded fusion cage;
d) an elongate expansion member; said expansion member being threaded and being threadedly received in said body bore; and
e) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration.

14. An anterior interbody device that is anteriorly variably expandable; said device comprising:
a) a U-shaped body having an upper wall and a lower wall hingeably joined by a rear wall; said body having a threaded bore, said upper and lower walls having a non-spaced configuration wherein anterior ends of said upper and lower walls are in close proximity to each other;
b) said upper and lower walls each having an anterior wedge mating receiver that face each other;
c) said upper and lower walls each including an anterior pair of spaced legs that respectively engage legs of the opposite wall when in non-expanded configuration and which define an aperture therebetween for receiving said expansion member into said body;
d) an elongate expansion member; said expansion member being threaded and being threadedly received in said body bore; and
e) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration.

15. The device according to claim 14 wherein:
a) said threaded bore is located in said rear wall of said device and during insertion of said expansion member into said bore, said expansion member extends longitudinally through said body from anterior end thereof into said threaded bore.

16. An anterior interbody device that is anteriorly variably expandable; said device comprising:
a) a U-shaped body having an upper wall and a lower wall hingeably joined by rear wall; said body having a threaded bore located in said rear wall, said upper and lower walls having a non-spaced configuration wherein anterior ends of said upper and lower walls are in close proximity to each other;

b) said upper and lower walls each having an anterior wedge mating receiver that face each other;

c) an elongate expansion member; said expansion member being threaded and being threadedly received in said body bore;

d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration;

e) said expansion member including a support surface anterior of said wedge surface; and f) said support surface being cylindrical in shape.

17. An anterior interbody device that is anteriorly variably expandable; said device comprising:

a) a U-shaped body having an upper wall and a lower wall hingeably joined by rear wall; said body having a threaded bore, said upper and lower walls having a non-spaced configuration wherein anterior ends of said upper and lower walls are in close proximity to each other;

b) said upper and lower walls each having an anterior wedge mating receiver that face each other;

c) an elongate expansion member; said expansion member being threaded and being threadedly received in said body bore;

d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration;

e) said expansion member having an axis of rotation;

f) said expansion member having a threaded region near a posterior end thereof that is mateable with said body bore; and g) said expansion member having a head near an anterior end thereof; said head including said wedge surface in the shape of a truncated cone; said head including a cylindrical supporting surface anterior of said wedge surface that is sized, shaped and positioned to engage and support said upper and lower walls when said expansion member is fully inserted into said body; so that as said expansion member is threadedly advanced into said body, said wedge surface engages said upper and lower wall wedge mating receivers and spreads the anterior ends of said upper and lower walls while hinging at a posterior end of said wall and, thereafter said support surface engages and supports said upper and lower walls in a preselected anterior spaced configuration.

18. An anterior interbody device that is anteriorly variably expandable; said device comprising:

a) a U-shaped body having an upper wall and a lower wall hingeably joined by a rear wall; said body having a threaded bore, said upper and lower walls having a non-spaced configuration wherein anterior ends of said upper and lower walls are in close proximity to each other;

b) said upper and lower walls each having an anterior end and an anterior wedge mating receiver that face each other;

c) an elongate expansion member; said expansion member being threaded and being threadedly received in said body bore;

d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration; said upper and lower anterior wedge mating receivers engaging and being supported by said expansion member at anterior ends of said walls after said anterior ends of said walls are placed in said spaced configuration; and wherein:

e) said expansion member includes a threaded shaft with an integral cylindrical head anteriorly positioned thereon with a wedge surface positional posterior of and adjacent to said head; said head being sized and positioned to engage and support said walls near the anterior ends thereof when said walls are in the spaced configuration.

19. An anterior interbody device that is anteriorly variably expandable; said device comprising:

a) a U-shaped body having an upper wall and a lower wall hingeably joined by a rear wall; said body having a threaded bore, said upper and lower walls having a non-spaced configuration wherein anterior ends of said upper and lower walls are in close proximity to each other;

b) said upper and lower walls each having an anterior end and an anterior wedge mating receiver that face each other;

c) an elongate expansion member; said expansion member being threaded and being threadedly received in said body bore;

d) said expansion member having an anterior wedge surface that is sized, shaped and positioned to engage said upper and lower anterior wedge mating receivers as said expansion member is threadedly advanced into said body bore, such that anterior ends of upper and lower walls are placed in a spaced configuration wherein said upper and lower walls become spaced greater than said non-spaced configuration; said upper and lower anterior wedge mating receivers engaging and being supported by said expansion member at the anterior ends of said walls in close proximity to a front of said device after said anterior ends of said walls are placed in said spaced configuration; and e) said expansion member including a threaded shaft with an integral cylindrical head anteriorly positioned thereon with a wedge surface positional posterior of and adjacent to said head; said head being sized and positioned to engage and support said walls near the anterior ends thereof, when said walls are in the spaced configuration.

* * * * *